United States Patent [19]
Connor et al.

[11] 4,098,998
[45] Jul. 4, 1978

[54] ALDEHYDE, OXIME AND PHENYLHYDRAZONE DERIVATIVES OF ACID S, AN ANTIBIOTIC PRODUCED BY *POLYANGIUM CELLULOSUM* VAR. *FULVUM*

[75] Inventors: David T. Connor, Parsippany; Samuel M. Ringel; Maximillian Von Strandtmann, both of Rockaway, all of N.J.

[73] Assignee: Warner-Lambert Company, Morris Plains, N.J.

[21] Appl. No.: 765,567

[22] Filed: Feb. 4, 1977

Related U.S. Application Data

[63] Continuation-in-part of Ser. No. 694,618, Jun. 10, 1976, abandoned.

[51] Int. Cl.$^2$ ............................................. C09B 23/00
[52] U.S. Cl. .................................. 542/447; 424/115; 424/121; 424/122
[58] Field of Search ................... 260/240 R; 424/115, 424/121, 122; 542/447

[56] References Cited

U.S. PATENT DOCUMENTS

| 3,651,216 | 3/1972 | Ringel et al. ......................... 424/115 |
| 3,804,948 | 4/1974 | Strandtmann et al. .............. 424/122 |
| 4,001,398 | 1/1977 | Connor et al. ....................... 424/122 |
| 4,009,261 | 2/1977 | Connor et al. ....................... 424/122 |
| 4,016,257 | 4/1977 | Connor et al. ....................... 424/122 |

*Primary Examiner*—Paul F. Shaver
*Attorney, Agent, or Firm*—Albert H. Graddis; Frank S. Chow; Anne M. Kelly

[57] ABSTRACT

The present invention relates to aldehyde, oxime and phenylhydrazone derivatives of the novel antibiotic substance, acid S, produced by the organism *Polyangium cellulosum* var. *fulvum* (ATCC No. 25532) and to processes for their preparation. The aldehyde, oxime and phenylhydrazone derivatives of acid S of this invention are useful as antifungal agents.

7 Claims, 3 Drawing Figures

ALDEHYDE S

FIG. 2 ALDEHYDE S OXIME

ALDEHYDE S PHENYL HYDRAZONE

ALDEHYDE, OXIME AND PHENYLHYDRAZONE DERIVATIVES OF ACID S, AN ANTIBIOTIC PRODUCED BY *POLYANGIUM CELLULOSUM* VAR. *FULVUM*

CROSS REFERENCE TO RELATED APPLICATIONS

This application is a continuation-in-part of U.S. Ser. No. 694,618, filed June 10, 1976, now abandoned.

SUMMARY OF THE INVENTION

The present invention relates to novel aldehyde, oxime and phenylhydrazone derivatives of acid S, a potent antibiotic produced by fermentation of the microorganism *Polyangium cellulosum* var. *fulvum* (ATCC No. 25532) in an appropriate culture medium. Specifically, the present invention relates to structural modifications of acid S having the following formula I:

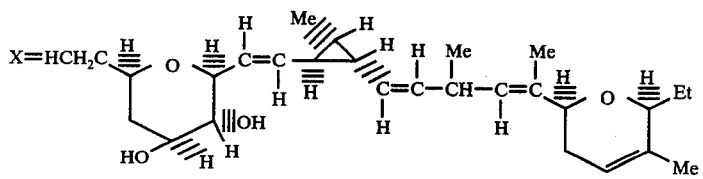

wherein X is oxygen, oxime or phenylhydrazone. The aldehyde S is prepared by converting acid S to the corresponding methyl ester with excess ethereal diazomethane, and reducing the acid S methyl ester to the corresponding aldehyde with diisobutylaluminum hydride. Aldehyde S is converted to the corresponding oxime with hydroxylamine hydrochloride; and the aldehyde S phenylhydrazone is obtained by reacting the aldehyde S with phenylhydrazine hydrochloride.

BRIEF DESCRIPTION OF THE DRAWINGS

The infrared spectra of representative 1-aldehyde, oxime and phenylhydrazone derivatives of this invention are illustrated in FIGS. 1, 2 and 3 of the drawings.

The novel aldehyde, oxime and phenylhydrazone derivatives of Acid S of this invention have the following formula I:

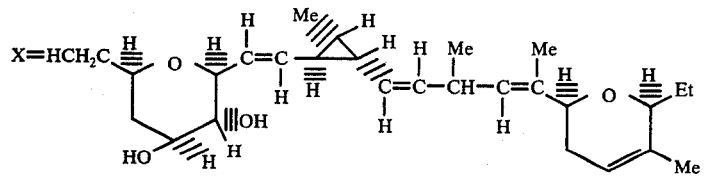

wherein X is oxygen, oxime or phenylhydrazone. The acid S molecule has the empirical formula $C_{28}H_{42}O_6$ and may be represented by the formula II:

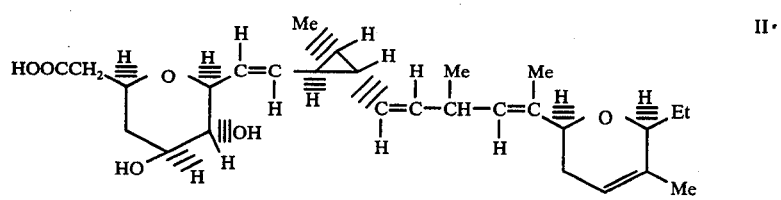

Thus, the aldehyde, oxime and phenylhydrazone derivatives of this invention are derivatives of the acid function in Acid S.

Acid S, as disclosed in U.S. Pat. No. 3,651,216, issued Mar. 21, 1972, and U.S. Pat. No. 3,804,948, issued Apr. 16, 1974, has the following characteristics:

Empirical Formula $C_{28}H_{42}O_6$, MW 474, infrared spectrum $\nu$870, 965, 1063, 1225, 1338, 1453, 1663, 1710, 2950, and 3400 cm.$^{-1}$, approximate $[\alpha]_D 25$ +36°, (chloroform, C=0.7), Rf 0.56 [silica gel, ethyl acetate:isopropanol:water (85:10:5)].

Acid S is a potent antifungal substance, elaborated when the microorganism *Polyangium cellulosum* var. *fulvum* (ATCC No. 25532) is fermented in a suitable culture medium. The aforementioned patent (U.S. Pat. No. 3,804,948) also describes the chemical preparation of the methyl ester of acid S. The methyl ester of acid S has the formula III:

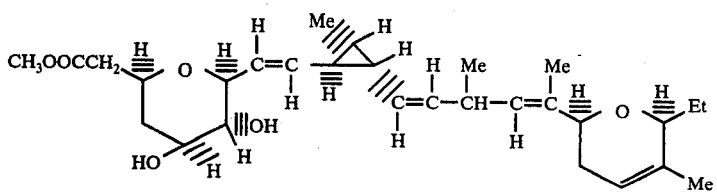

and the following characteristics:

Empirical Formula $C_{29}H_{44}O_6$, MW 488, infrared spectrum $\nu$ 860, 965, 1060, 1200, 1250, 1370, 1440, 1518, 1658, 1725, 2900, and 3400 cm.$^{-1}$, Rf 0.56 [silica gel, ethyl acetate:cyclohexane (4:1)].

The organism designated *Polyangium cellulosum* var. *fulvum* is deposited at the American Type Culture Collection, and identified as ATCC #25532. All restriction on the availability of the culture deposit at ATCC will be irrevocably removed upon issuance of the instant application. The culture at ATCC will be maintained throughout the effective life of the patent.

According to the subject invention, the aldehyde of acid S is prepared by converting acid S to the corresponding methyl ester with excess ethereal diazomethane, and reducing the acid S methyl ester to the corresponding aldehyde with diisobutylaluminum hydride. Aldehyde S is converted to the corresponding oxime with hydroxylamine hydrochloride; and the aldehyde S phenylhydrazone is obtained by reacting the aldehyde S with phenylhydrazine hydrochloride.

Figure 1:
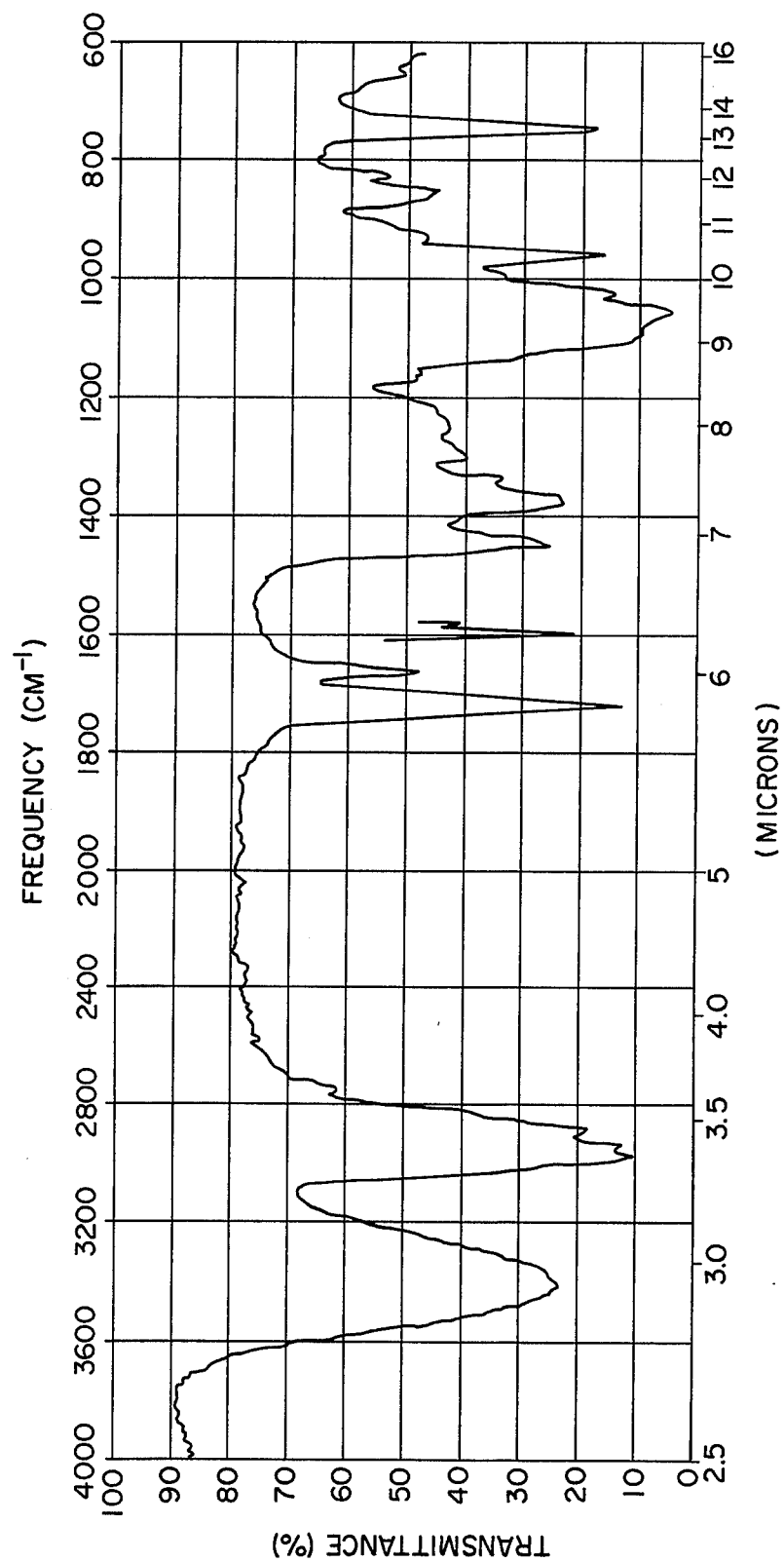
FIG. 1 depicts the infrared spectrum of aldehyde S.

Thus, to prepare the aldehyde S of this invention, about 2.5 equivalents of diisobutylaluminum hydride in from about 10 to about 200 equivalents, preferably about 20 equivalents of hexane, are added to one equivalent of acid S methyl ester ($C_{29}H_{44}O_6$) in from about 50 to about 300 equivalents (preferably about 100 equivalents) of toluene. The reaction is conducted in an inert atmosphere, preferably under nitrogen, at a temperature of from about −78° to about −40° C., preferably at about −78° C. The reaction goes to completion in a relatively short period of time, typically in about five minutes. The aldehyde S obtained has an empirical formula of $C_{28}H_{42}O_5$ and an infrared spectrum as shown in FIG. 1.

Figure 2:
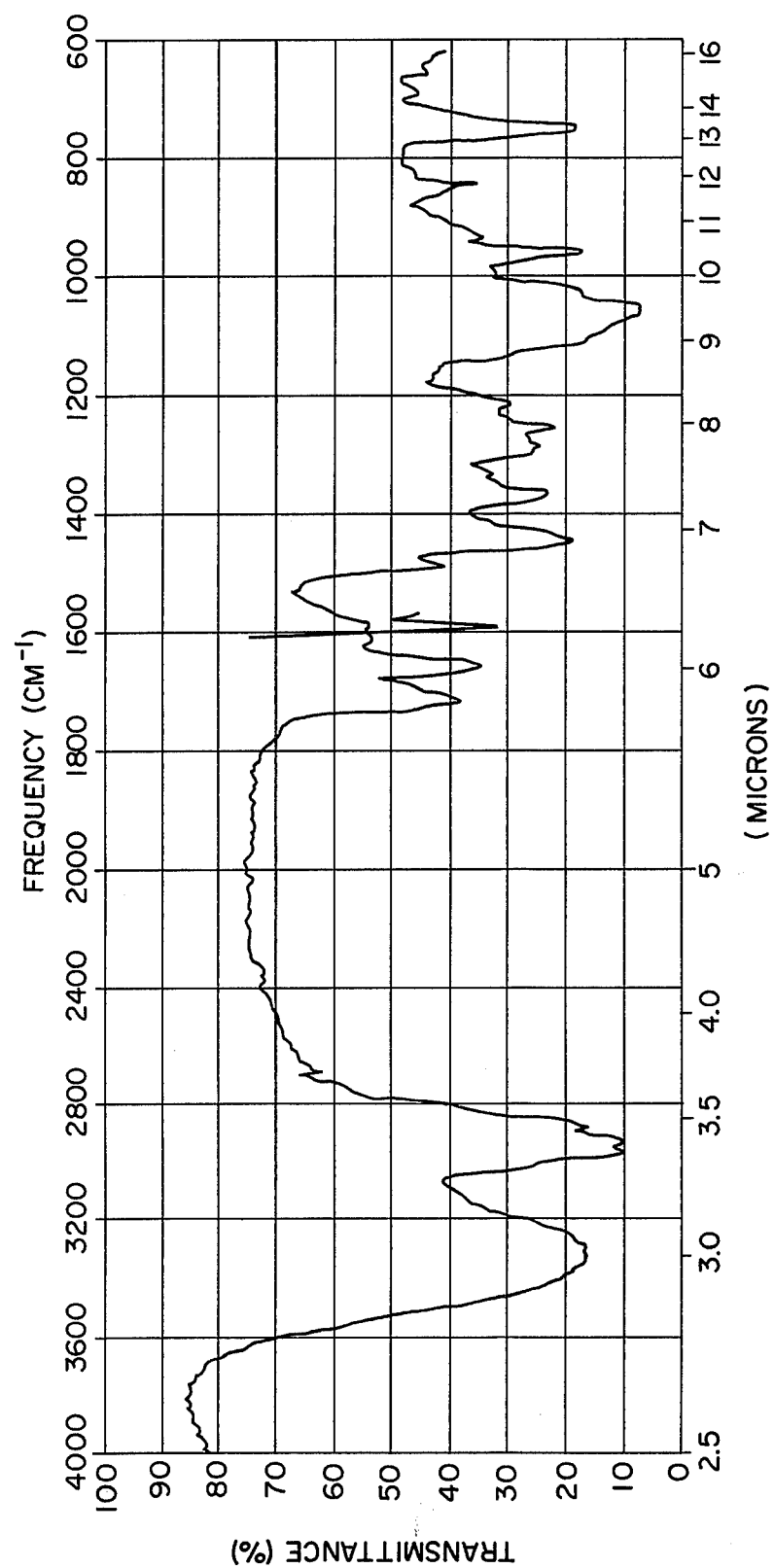
FIG. 2 depicts the infrared spectrum of aldehyde S oxime.

To obtain aldehyde S oxime, one equivalent of aldehyde S is reacted with from about one to about two equivalents, preferably about 1.5 equivalents, of hydroxylamine hydrochloride; from about 0.5 to about two equivalents of sodium acetate; in from about 500 to about 2,000 equivalents of ethanol and from about 100 to about 1,000 equivalents of water. This reaction is conducted at reflux temperature, preferably in an inert atmosphere such as nitrogen, for at least two hours to allow the reaction to go to completion. The aldehyde S oxime obtained has the empirical formula $C_{28}H_{43}NO_5$ and an infrared spectrum as shown in FIG. 2.

Figure 3:
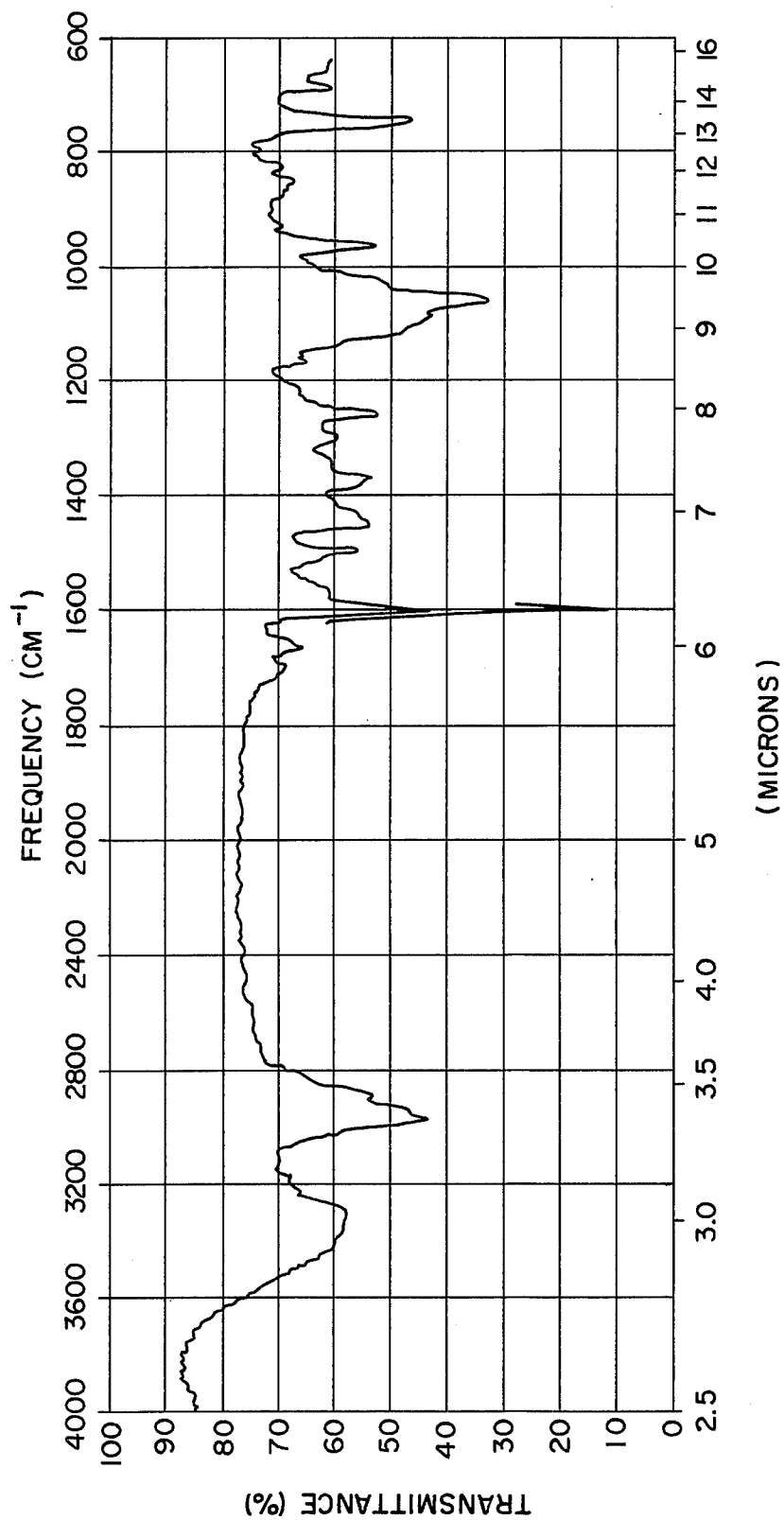
FIG. 3 depicts the infrared spectrum of aldehyde S phenylhydrazone.

To obtain the aldehyde S phenylhydrazone of the invention, one equivalent of aldehyde S is reacted with about one equivalent of phenylhydrazine hydrochloride and from about 0.5 to about one equivalent of sodium acetate in from about 500 to about 2,000 equivalents of ethanol and from about 100 to about 1,000 equivalents of water. The reaction is conducted at reflux temperature, preferably in an inert atmosphere such as nitrogen, for at least three hours to allow the reaction to go to completion. The aldehyde S phenylhydrazone obtained has an empirical formula of $C_{34}H_{48}N_2O_4$ and an infrared spectrum as shown in FIG. 3.

The compounds of the present invention are characterized by infrared spectroscopy and mass spectrometry. The infrared spectra of the 1-aldehyde, oxime and phenylhydrazone derivatives of acid S of this invention are determined as thin films with an infrared absorption spectrometer equipped with a diffraction grating. In addition to providing spectral evidence for the chemical transformations of the processes of this invention, the infrared spectra of the compounds of this invention represent characteristic physical properties useful for their identification.

The mass spectra of the 1-aldehyde, oxime and phenylhydrazone derivatives of acid S of this invention are measured on a double-focusing high resolution mass spectrometer utilizing a heated direct insertion probe. The molecular composition of the parent peaks are determined by employing perfluorotributylamine (mass spectral grade, available from PCR, Inc., Gainsville, Florida) as the internal standard and peak matching techniques well-known to those skilled in the art. The application of these mass spectral techniques permits not only the determination of the molecular composition of the parent ion and confirmation of the postulated transformations, but, like the aforementioned infrared measurements, provides a definitive physical property useful for identification purposes.

The novel aldehyde, oxime and phenylhydrazone derivatives of this invention inhibit the growth of fungi, such as of yeast phase of *Histoplasma capsulatum*, and *Microsporum fulvum*. Minimum inhibitory concentrations falling within the range of 0.78 to 0.098 micrograms/milliliter, are obtained when evaluated by the *in vitro* tube dilution technique described in U.S. Pat. No. 3,651,216. Thus, the compounds of the present invention are useful for the treatment of dermatophytic and systemic fungal disease.

The antifungal substances of this invention can be formulated with inert excipients into various dosage forms for oral, parenteral and topical administration by methods well known to those skilled in the pharmacist's art. Tablets, capsules, powders, solutions, suspensions, ointments, gels and creams are included among these dosage forms.

The aldehyde, oxime and phenylhydrazone derivatives of acid S of this invention can be administered orally, parenterally or topically to various mammals, such as dogs, cats and guinea pigs, afflicted with fungal disease. The typical dose is about 0.01 to 100 mg/kg of body weight of the animal.

The following examples are included to further illustrate the invention and are not to be construed as limiting the scope of the invention:

EXAMPLE 1

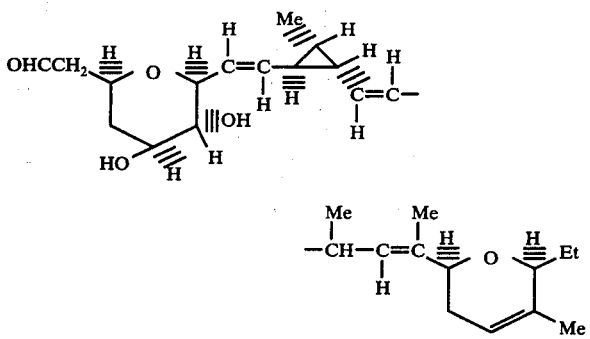

Aldehyde S. A solution of diisobutyl aluminum hydride (142 mg, 2.5 equivalents) in hexane (0.7 ml) is added to a solution of Acid S methyl ester (195.2 mg, 1 equivalent) in toluene (5 ml) at −78° C. under nitrogen with stirring. The reaction mixture is stirred at −78° C. for 5 minutes and then partitioned between ether and 2N hydrochloric acid. The ether extracts are dried over $MgSO_4$ and evaporated to give a colorless oil. The product is purified by preparative thin layer chromatography to give a colorless oil (104 mg, 56%). Diagnostic tlc indicates a pure homogeneous product.

Empirical formula, $C_{28}H_{42}O_5$

Molecular weight, 458

Infrared Spectrum, $\nu$max 3600–3200cm$^{-1}$(OH), 1730 (CO of —CHO).

Mass Spectrum.

Observed molecular ion — 458.2941

Calculated for $C_{28}H_{42}O_5$ — 458.3032 m/e (relative intensity) 458 (6), 440 (4), 429 (33), 411 (3), 393 (3), 363 (5), 345 (12), 327 (8), 299 (7), 263 (17) and 193 (100).

EXAMPLE 2

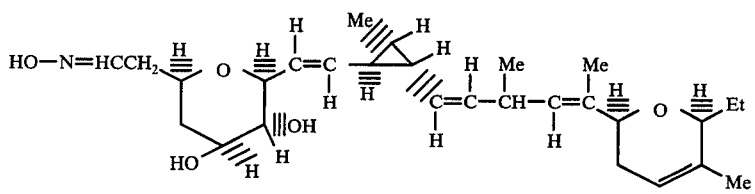

Aldehyde S oxime. A mixture of aldehyde S (8 mg), hydroxylamine hydrochloride (2 mg) and sodium acetate (1 mg) in ethanol (7 ml) and water (1 ml) is refluxed under nitrogen for 2 hours. The solvents are evaporated under reduced pressure. The product is isolated using preparative thin layer chromatography as a colorless gum (9 mg, 100%).

Empirical Formula, $C_{28}H_{43}NO_5$

Molecular weight, 473

Infrared Spectrum, $\nu$max 3600–3100cm$^{-1}$ (OH).

Mass Spectrum.

Observed molecular ion — 473.3021

Calculated for $C_{28}H_{43}NO_5$ — 473.2998 m/e (relative intensity) 473 (8), 456 (20), 444 (10), 426 (14), 378 (7), 360 (11), 298 (8), 278 (11), 260 (11) and 193 (100).

EXAMPLE 3

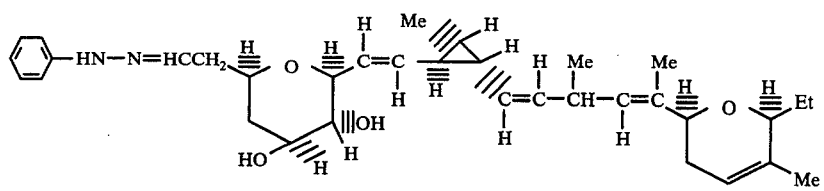

Aldehyde S phenylhydrazone. A mixture of aldehyde S (9.16 mg, 1 equivalent), phenylhydrazine hydrochloride (2.89 mg, 1 equivalent) and sodium acetate (1 mg) in ethanol (4 ml) and water (1 ml) is refluxed under nitrogen for 3 hours. The solvents are evaporated under reduced pressure to give a yellow residue. The product is extracted from the residue with $CHCl_3$. The $CHCl_3$ is evaporated to give a yellow oil (10 mg, 90%).

Empirical formula, $C_{34}H_{48}N_2O_4$

Molecular weight, 548

Infrared Spectrum, $\nu$max 3600 to 3100 (OH and NH), 1600 (aromatic).

Mass Spectrum.

Observed molecular ion — 548.3641

Calculated for $C_{34}H_{48}N_2O_4$ — 548.3614 m/e (relative intensity) 548 (1), 299 (10) and 193 (100).

We claim:

1. A compound having the formula I:

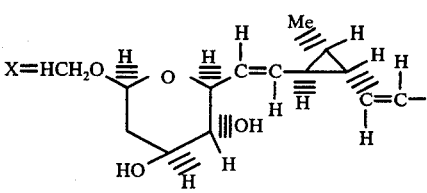

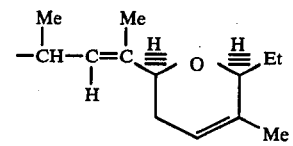

wherein X is oxygen, oxime or phenylhydrazone, said compound being derived from the antibiotic acid S.

2. A compound according to claim 1 which is aldehyde S having the formula:

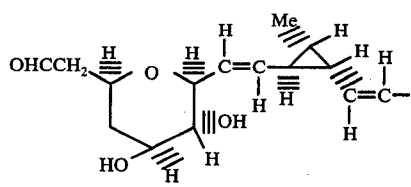

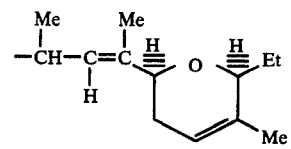

3. A compound according to claim 1 which is aldehyde S oxime having the formula:

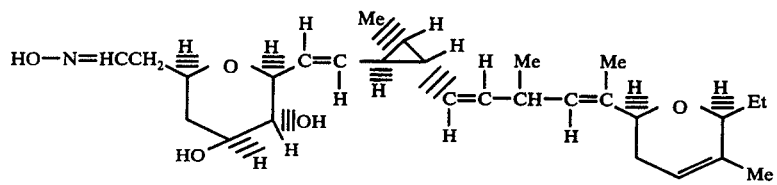

4. A compound according to claim 1 which is aldehyde S phenylhydrazone.

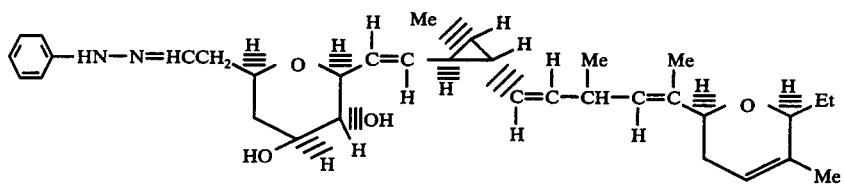

5. A process for preparing aldehyde S having the formula:

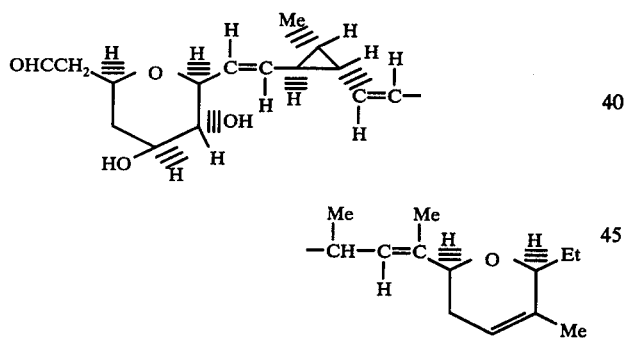

which comprises reacting one equivalent of acid S methyl ester ($C_{29}H_{44}O_6$) having the following formula III:

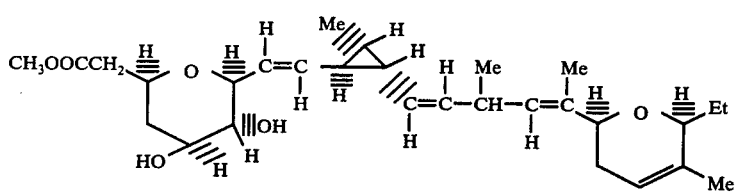

in from about 10 to about 200 equivalents of hexane, with about 2.5 equivalents of diisobutyl aluminum hydride in from about 50 to about 300 equivalents of toluene in an inert atmosphere at a temperature of from about −78° C. to about −40° C.

6. A process for preparing aldehyde S oxime having the formula:

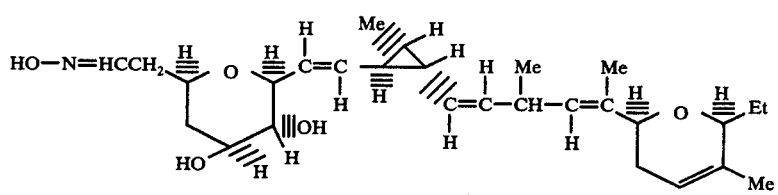

which comprises reacting one equivalent of aldehyde S ($C_{28}H_{42}O_5$) having the following structural formula:

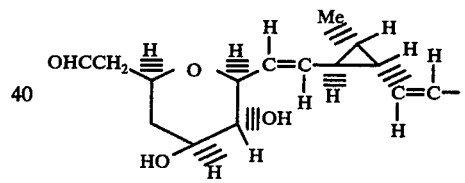

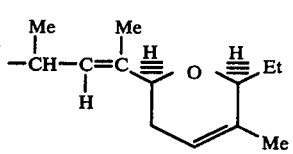

with from about one to about two equivalents of hydroxylamine hydrochloride; from about 0.5 to about 2 equivalents of sodium acetate; in from about 500 to about 2,000 equivalents of ethanol and from about 100 to about 1,000 equivalents of water, at reflux temperature for at least two hours.

7. A process for preparing aldehyde S phenylhydrazone having the formula:

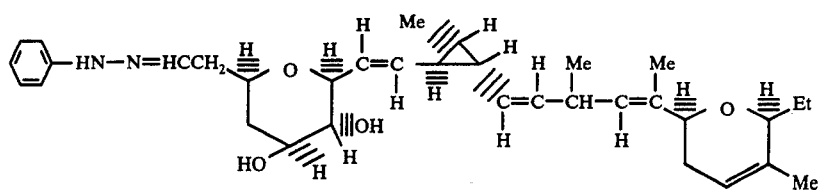

which comprises reacting one equivalent of aldehyde S ($C_{28}H_{42}O_5$) having the following structural formula:

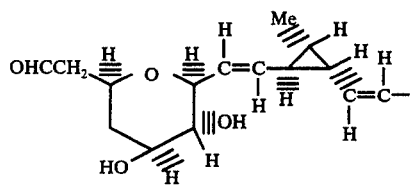

-continued

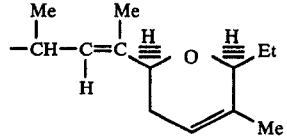

with one equivalent of phenylhydrazine hydrochloride and from about 0.5 to about 1 equivalent of sodium acetate in from about 500 to about 2,000 equivalents of ethanol and from about 100 to about 1,000 equivalents of water, at reflux temperature for at least three hours.

* * * * *